(12) United States Patent
Jiang et al.

(10) Patent No.: US 12,347,213 B2
(45) Date of Patent: Jul. 1, 2025

(54) METHOD AND APPARATUS FOR OBTAINING FEATURE OF DUCT TISSUE BASED ON COMPUTER VISION, AND INTELLIGENT MICROSCOPE

(71) Applicant: TENCENT TECHNOLOGY (SHENZHEN) COMPANY LIMITED, Guangdong (CN)

(72) Inventors: Cheng Jiang, Guangdong (CN); Jiarui Sun, Guangdong (CN); Liang Wang, Guangdong (CN); Rongbo Shen, Guangdong (CN); Jianhua Yao, Guangdong (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 453 days.

(21) Appl. No.: 17/685,099

(22) Filed: Mar. 2, 2022

(65) Prior Publication Data
US 2022/0319208 A1    Oct. 6, 2022

Related U.S. Application Data

(63) Continuation of application No. PCT/CN2020/126102, filed on Nov. 3, 2020.

(30) Foreign Application Priority Data

Feb. 21, 2020   (CN) .......................... 202010108133.6

(51) Int. Cl.
*G06T 7/11*   (2017.01)
*A61B 90/20*  (2016.01)
(Continued)

(52) U.S. Cl.
CPC ............ *G06V 20/695* (2022.01); *A61B 90/20* (2016.02); *G02B 21/365* (2013.01);
(Continued)

(58) Field of Classification Search
None
See application file for complete search history.

(56) References Cited

U.S. PATENT DOCUMENTS

2006/0002608 A1    1/2006  Haddon et al.
2006/0127880 A1*   6/2006  Harris .................... G06V 20/69
                                                        382/128
(Continued)

FOREIGN PATENT DOCUMENTS

CN    102177435 A    9/2011
CN    106611413 A    5/2017
(Continued)

OTHER PUBLICATIONS

B, Archana. "Breast Histology." Holistic Approach to Breast Disease. Singapore: Springer Nature Singapore. (2023): 23-27. Web. (Year: 2023).*

(Continued)

*Primary Examiner* — Amandeep Saini
*Assistant Examiner* — Caroline Tabancay Duffy
(74) *Attorney, Agent, or Firm* — ArentFox Schiff LLP

(57) ABSTRACT

Aspects of the disclosure are directed to the field of artificial intelligence technologies and provides a method and an apparatus for obtaining a feature of duct tissue based on computer vision, an intelligent microscope, a storage medium, and a computer device. The method can include the steps of obtaining an image including duct tissue, determining, in an image region corresponding to the duct tissue in the image, at least two feature obtaining regions adapted to duct morphology of the duct tissue, obtaining cell features of cells of the duct tissue in the feature obtaining regions respectively, and obtaining a feature of the duct tissue based on the cell features of the cells of the duct tissue in the feature obtaining regions respectively.

18 Claims, 8 Drawing Sheets

(51) Int. Cl.
| | |
|---|---|
| *G02B 21/36* | (2006.01) |
| *G06T 7/00* | (2017.01) |
| *G06T 7/13* | (2017.01) |
| *G06T 7/155* | (2017.01) |
| *G06V 10/22* | (2022.01) |
| *G06V 10/44* | (2022.01) |
| *G06V 20/69* | (2022.01) |

(52) U.S. Cl.
CPC .............. *G06T 7/0012* (2013.01); *G06T 7/11* (2017.01); *G06T 7/13* (2017.01); *G06T 7/155* (2017.01); *G06V 10/22* (2022.01); *G06V 10/44* (2022.01); *G06V 20/698* (2022.01); *A61B 2576/02* (2013.01); *G06T 2207/10056* (2013.01); *G06T 2207/20021* (2013.01); *G06T 2207/30004* (2013.01); *G06T 2207/30096* (2013.01); *G06T 2207/30242* (2013.01); *G06V 2201/03* (2022.01)

(56) References Cited

U.S. PATENT DOCUMENTS

| | | | | |
|---|---|---|---|---|
| 2011/0170754 | A1* | 7/2011 | Yoshihara | G06T 7/0012 |
| | | | | 382/128 |
| 2013/0051650 | A1* | 2/2013 | Santamaria-Pang ... | G16B 40/20 |
| | | | | 382/133 |
| 2016/0070949 | A1* | 3/2016 | Tunstall | G06V 20/69 |
| | | | | 382/133 |
| 2016/0188800 | A1 | 6/2016 | Stopek | |
| 2019/0353644 | A1 | 11/2019 | Vidi et al. | |
| 2020/0160097 | A1* | 5/2020 | Jaber | G06T 7/0012 |
| 2022/0058801 | A1* | 2/2022 | Klimov | G06T 7/0012 |

FOREIGN PATENT DOCUMENTS

| | | |
|---|---|---|
| CN | 107330263 A | 11/2017 |
| CN | 111339899 A | 6/2020 |

OTHER PUBLICATIONS

De Marco, Federica, Rozenn Le Hir, and Sylvie Dinant. "The Rendez-Vous of Mobile Sieve-Element and Abundant Companion-Cell Proteins." Current opinion in plant biology 43 (2018): 108-112. Web. (Year: 2018).*

Frenzel, Peter, Judith Ewald, and Anna Pint. "Salinity-Dependent Sieve Pore Variability in Cyprideis Torosa; an Experiment." Journal of micropalaeontology 36.1 (2017): 57-62. Web. (Year: 2017).*

Schiffhauer LM, Boger JN, Bonfiglio TA, Zavislan JM, Zuley M, Fox CA. Confocal microscopy of unfixed breast needle core biopsies: a comparison to fixed and stained sections. BMC Cancer. Aug. 3, 2009;9:265. doi: 10.1186/1471-2407-9-265. PMID: 19650910; PMCID: PMC3087331. (Year: 2009).*

Supplementary European Search Report issued Oct. 31, 2022 in Application No. 20920584.8, p. 1-7.

International Search Report dated Feb. 3, 2021 issued in corresponding application PCT/CN2020/126102 (with English translation).

Office Action received for European Patent Application No. 20920584.8, mailed on Jan. 3, 2025, 6 pages.

Tao et al., "Assessment of breast pathologies using nonlinear microscopy", Proceedings of the National Academy of Sciences (PNAS), vol. 111, No. 43, Oct. 13, 2014, pp. 15304-15309.

\* cited by examiner

METHOD AND APPARATUS FOR OBTAINING FEATURE OF DUCT TISSUE BASED ON COMPUTER VISION, AND INTELLIGENT MICROSCOPE

RELATED APPLICATION

This application is a continuation of International Application No. PCT/CN2020/126102, filed on Nov. 3, 2020, which claims priority to Chinese Patent Application No. 202010108133.6, entitled "METHOD AND APPARATUS FOR OBTAINING FEATURE OF DUCT TISSUE BASED ON COMPUTER VISION, AND INTELLIGENT MICROSCOPE" filed on Feb. 21, 2020. The entire disclosures of the prior applications are hereby incorporated by reference in their entirety.

FIELD OF THE TECHNOLOGY

This application relates to the field of artificial intelligence technologies, including a method and an apparatus for obtaining a feature of duct tissue based on computer vision, an intelligent microscope, a computer-readable storage medium, and a computer device.

BACKGROUND OF THE DISCLOSURE

With the development of artificial intelligence technologies, an image classification and processing technology based on the artificial intelligence technologies has emerged. In this technology, the artificial intelligence technologies can be applied to performing processing, such as feature extraction, identification, and classification, on duct tissue, such as breast duct tissue, in images.

An image of duct tissue may be obtained by segmenting the duct tissue in an image. A related feature of the duct tissue may be extracted based on the image of the duct tissue. In an existing duct tissue feature extraction technology, an overall quantity of nuclei of the duct tissue in the image is mainly used as a main feature of the duct tissue. However, the overall quantity of nuclei in the duct tissue is usually relatively large and difficult to count. Accordingly, it is difficult for the overall quantity of nuclei to reflect the feature of the duct tissue accurately, resulting in relatively low accuracy in obtaining the feature of the duct tissue using this technology.

SUMMARY

According to various embodiments provided in this application, a method and an apparatus for obtaining a feature of duct tissue based on computer vision, an intelligent microscope, a non-transitory computer-readable storage medium, and a computer device are provided.

An embodiment of the present disclosure provides a method for obtaining a feature of duct tissue based on computer vision. The method can include obtaining an image that includes duct tissue, and determining at least two feature obtaining regions that are adapted to duct morphology of the duct tissue in an image region corresponding to the duct tissue in the image. The method can further include obtaining cell features of cells of the duct tissue in the at least two feature obtaining regions, respectively, and obtaining a feature of the duct tissue based on the cell features in the at least two feature obtaining regions.

Aspects of the disclosure can further include, before the determining the at least two feature obtaining regions adapted to duct morphology of the duct tissue, using a boundary of the image region corresponding to the duct tissue in the image as a boundary of a duct tissue region, and determining the duct morphology of the duct tissue based on a boundary shape of the boundary of the duct tissue region.

Further embodiments of the disclosure are directed to an intelligent microscope, including an image acquisition device and an image analysis device. The image acquisition device can be configured to obtain an image comprising duct tissue and transmit the image to the image analysis device. Additionally, the image analysis device can be configured to perform the operations of the method according described above.

Other aspects of the disclosure are directed to an apparatus for obtaining a feature of duct tissue based on computer vision. The apparatus can include processing circuitry that is configured to obtain an image including duct tissue, determine at least two feature obtaining regions adapted to duct morphology of the duct tissue in an image region corresponding to the duct tissue in the image, obtain cell features of cells of the duct tissue in the at least two feature obtaining regions, respectively and obtain a feature of the duct tissue based on the cell features in the at least two feature obtaining regions.

Additionally, embodiments described in the disclosure are directed to a non-transitory computer-readable storage medium that stores instructions which, when executed by a processor, cause the processor to perform operations that include obtaining an image that includes duct tissue, determining at least two feature obtaining regions that are adapted to duct morphology of the duct tissue in an image region corresponding to the duct tissue in the image, obtaining cell features of cells of the duct tissue in the at least two feature obtaining regions, respectively, and obtaining a feature of the duct tissue based on the cell features in the at least two feature obtaining regions.

BRIEF DESCRIPTION OF THE DRAWINGS

Various exemplary embodiments of this disclosure that are proposed as examples will be described in detail with reference to the following figures, wherein like numerals reference like elements, and wherein.

DESCRIPTION OF EMBODIMENTS

Figure 1:
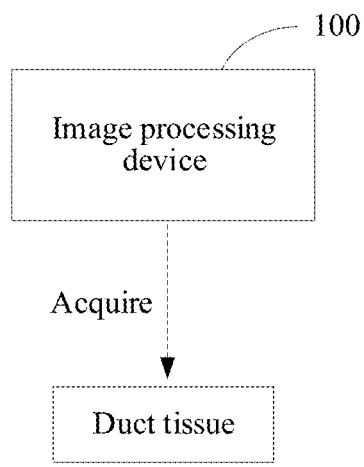
FIG. 1 is a diagram of an application environment of a method for obtaining a feature of duct tissue based on computer vision according to an embodiment.

To make objectives, technical solutions, and advantages of this application clearer and more comprehensible, this application is further described in detail with reference to the accompanying drawings and embodiments. It is to be understood that the specific embodiments described herein are only used for explaining this application, and are not used for limiting this application.

Artificial intelligence (AI) is a theory, method, technology, and application system in which a digital computer or a machine controlled by a digital computer is used to simulate, extend, and expand human intelligence, sense an environment, acquire knowledge, and use the knowledge to obtain an optimal result. In other words, the AI is a comprehensive technology of computer science, which attempts to understand essence of intelligence and produces a new intelligent machine that can respond in a manner similar to human intelligence. The AI is to study the design principles and implementation methods of various intelligent machines, to enable the machines to have the functions of perception, reasoning, and decision-making.

The AI technology is a comprehensive discipline, covering a wide range of fields including both a hardware-level technology and a software-level technology. Basic AI technologies generally include technologies, such as sensors, dedicated AI chips, cloud computing, distributed storage, big data processing technologies, operating and interaction systems, and mechatronics. AI software technologies mainly include several major directions such as a computer vision, a speech processing technology, a natural language processing technology, and machine learning and deep learning.

Computer vision (CV) is a science that studies how to use a machine to "see", and furthermore, that uses a camera and a computer to replace human eyes to perform machine vision, such as identification, tracking, and measurement on an object. Computer vision can further perform graphic processing, so that the computer processes the object into an image more suitable for human eyes to observe, or an image transmitted to an instrument for detection. As a scientific discipline, computer vision studies related theories and technologies and attempts to establish an AI system that can obtain information from images or multidimensional data. The computer vision generally includes technologies, such as image processing, image identification, image semantic understanding, image retrieval, OCR, video processing, video semantic understanding, video content/behavior recognition, three-dimensional object reconstruction, a 3D technology, virtual reality, augmented reality, synchronous positioning, and map construction, and further include biometric feature recognition technologies such as common face recognition and fingerprint recognition.

In the method for obtaining a feature of duct tissue based on computer vision provided by this application, computer vision in the AI technologies can be applied to rapid and accurate feature extraction of duct tissue in an image. Furthermore, based on the feature extraction of the duct tissue, the AI technologies may be further applied to accurately identifying and classifying the duct tissue, thereby implementing the classification of the feature of the duct tissue with the help of computer vision.

Specifically, referring to FIG. 1, a method for obtaining a feature of duct tissue based on computer vision provided by this application may be applied to an application environment shown in FIG. 1. FIG. 1 is a diagram of an application environment of a method for obtaining a feature of duct tissue based on computer vision according to an embodiment. The application environment may include an image processing device 100. The image processing device 100 may be a computer device that has image processing capabilities, such as image acquisition, analysis, and display. The computer device may be specifically at least one of a mobile phone, a tablet computer, a desktop computer, or a laptop computer. Therefore, based on the image processing capabilities, such as image acquisition and analysis, of the image processing device 100, computer vision may be applied to feature extraction of duct tissue through the image processing device 100. The image processing device 100 may acquire an image of the duct tissue, for example, locate a position of the duct tissue in the image based on a contour of the duct tissue, so as to further perform image processing, such as feature extraction and classification on the duct tissue in the image.

In addition, the image processing device 100 may be specifically an intelligent microscope. The intelligent microscope incorporates visual, voice, and natural language processing technologies, and an augmented reality (AR) technology of the AI. A user may input a control instruction, such as a voice instruction, to the intelligent microscope. The intelligent microscope may perform an operation, such as automatic identification, detection, quantitative calculation, and report generation, according to the instruction, or may display a detection result in real time in a field of view shown in an eyepiece viewed by the user, and remind the user in time without disturbing a film reading process of the user, thereby improving processing efficiency and accuracy. That is, the duct tissue may be placed under an intelligent microscope. The intelligent microscope may automatically adjust a zoom factor of a lens to acquire an image of the duct tissue, and may further identify the duct tissue from the acquired image to segment an image including the duct tissue, automatically classify the duct tissue according to a feature of the duct tissue, and display automatic classification results in the form of different color labels in the field of view of an eyepiece viewed by the user, thereby labeling the type of the correspondingly classified duct tissue in the field of view to assist the user in viewing an image of a pathological slide or the like of the duct tissue, on the intelligent microscope.

Specifically, in the method for obtaining a feature of duct tissue based on computer vision provided by this application, the image processing device 100 may acquire an image including duct tissue through scanning or the like. Then, the image processing device 100 may determine, in an image region corresponding to the duct tissue in the image, at least two feature obtaining regions adapted to duct morphology of the duct tissue. Next, the image processing device 100 obtains cell features of cells of the duct tissue in the at least two feature obtaining regions respectively. Last, the image processing device 100 may obtain a feature of the duct tissue based on the cell features in the at least two feature obtaining regions. The method may be applied to an image processing device 100, such as a computer device or an intelligent microscope, to accurately obtain a feature of duct tissue for the duct tissue in various shapes included in, for example, the pathological slide image.

In the application scenario shown in FIG. 1, the image processing device 100 may be used for locally scanning the duct tissue and obtaining a feature from the duct tissue in various shapes in an image obtained by means of scanning. In addition, the feature of the duct tissue may be obtained in a remote communication manner. Exemplarily, the feature of the duct tissue may be obtained non-locally based on a fifth-generation mobile communication technology (5th generation mobile networks or 5th generation wireless systems, 5th generation, 5G or 5G technology for short). A user may acquire an image including duct tissue by using a terminal device, such as a mobile phone or a tablet computer, and then transmit the image to a remote image processing device 100 in real time based on a 5G communication network. Then, the image processing device 100 may obtain a feature from the duct tissue in the image, and transmit a feature obtaining result to a terminal device of the user by using the 5G communication network, so that the user may learn of the feature obtaining result by using the terminal device. Because of advantages of the 5G communication technology, such as a strong real-time characteristic, even if feature extraction is performed on by the remote image processing device 100 the duct tissue in the image acquired by the user onsite, the user can still be enabled to obtain a corresponding duct tissue feature extraction result in real time onsite, so image data processing pressure at the user end can be reduced while ensuring the real-time performance.

Figure 2:
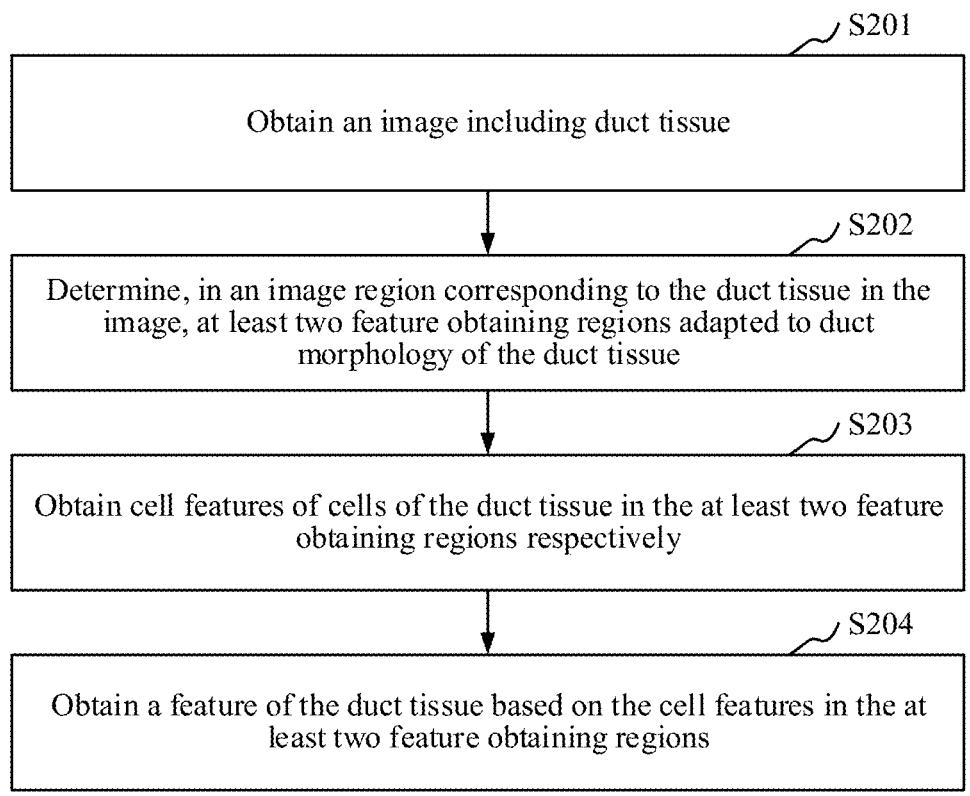
FIG. 2 is a schematic flowchart of a method for obtaining a feature of duct tissue based on computer vision according to an embodiment.

In an embodiment, a method for obtaining a feature of duct tissue based on computer vision is provided. FIG. 2 is a schematic flowchart of a method for obtaining a feature of duct tissue based on computer vision according to an embodiment. This embodiment is mainly described by using an example in which the method is applied to the image processing device 100 in FIG. 1. For the foregoing description of the image processing device 100 in FIG. 1, the image processing device 100 may be specifically a computer device, such as a mobile phone, a tablet computer, a desktop computer, or a laptop computer, that has image processing capabilities such as image acquisition, analysis, and display. Referring to FIG. 2, the method specifically includes the following steps:

In Step S201, the method can obtain an image including duct tissue. In this step, the image processing device 100 acquires an image including duct tissue in real time in a manner such as scanning the duct tissue, or may obtain an image including duct tissue pre-stored on an electronic device such as a mobile phone or a desktop computer. The image may be a pathological slide image of the duct tissue. The pathological slide image may be obtained by obtaining a specific size of pathological duct tissue and making the pathological duct tissue into a pathological slide using a histopathology method. The pathological slide image may alternatively be processed through HE staining to form an HE pathological slide image including the duct tissue. HE staining processing refers to a hematoxylin-eosin staining method (HE staining method for short), so that a nucleus and cytoplasm, and the like in the duct tissue may be colored, to facilitate identification and feature extraction of the duct tissue in the image. In addition, the image including the duct tissue obtained by the image processing device 100 may further include a binarized or multivalued image. For binarization, the duct tissue may be distinguished from an image background. For example, a pixel value of the duct tissue is set to 1, and a pixel value of the image background is set to 0, which is convenient for identifying the duct tissue and a contour feature thereof from the image.

In Step S202, the method can determine, in an image region corresponding to the duct tissue in the image, at least two feature obtaining regions adapted to duct morphology of the duct tissue. In this step, the image processing device 100 may first determine the image region corresponding to the duct tissue in the image, and may generally use, in the image including the duct tissue, an entire region enclosed by a boundary of the duct tissue as an image region corresponding to the duct tissue in the image. The image processing device 100 may divide feature obtaining regions in the image region. The feature obtaining region is mainly used for extracting cell features of cells of the duct tissue in the feature obtaining region. The quantity of the feature obtaining regions needs to be at least two. That is, the image processing device 100 needs to select, in the image region corresponding to the duct tissue in the image, at least two feature obtaining regions, to respectively obtain cell features of cells of the duct tissue in the two regions.

The selection of the feature obtaining regions also needs to be adapted to duct morphology of the duct tissue, to adaptively select a feature obtaining region adapted to the duct morphology of the duct tissue for different proliferation types or growth patterns of the duct and adapting to differences in the duct morphology. For example, for duct tissue with circular duct morphology, circular regions corresponding to different radii with the duct tissue as a center may be selected as the feature obtaining regions or the like. Moreover, at least two feature obtaining regions may be selected to facilitate comparing different features, such as the cell features of the duct tissue, in different feature obtaining regions, to accurately obtain the feature of the duct tissue. Therefore, the image processing device 100 may adaptively select at least two feature obtaining regions according to the duct morphological characteristic of the duct tissue.

In Step S203, the method can obtain cell features of cells of the duct tissue in the at least two feature obtaining regions respectively. In this step, the image processing device 100 needs to obtain, in feature obtaining regions, cell features of cells of the duct tissue respectively in corresponding regions. Before the image processing device 100 extracts the cell features, which cell features need to be extracted may be first determined. Moreover, to more accurately determine the feature of the duct tissue, the types of the extracted cell features may be same in respective feature obtaining regions. That is, if the cell features extracted by the image processing device 100 in a feature obtaining region A include a cell feature X and a cell feature Y, the image processing device 100 also extracts a cell feature X and a cell feature Y in a feature obtaining region B.

For the types of the cell features, exemplarily, in an embodiment, the cell features of cells of the duct tissue in the at least two feature obtaining regions respectively may include at least one of a cell statistical feature or a cell structural feature of cells in a corresponding feature obtaining region. The cell structural feature is a basic feature for a single cell. For example, a shape, a size, a color, and the like may all be used as cell structural features. Moreover, the cell statistical feature is an overall feature of a plurality of cells in the corresponding feature obtaining region. For example, in the corresponding feature obtaining region, the density and distribution of the cells may be obtained. In addition, the cell statistical features, such as an average value and variance of nucleus sizes and an average value and variance of cell circularity, may further be obtained respectively in the feature obtaining region.

In a specific application, the image processing device 100 may obtain a size, circularity, or density of a nucleus in a feature obtaining region as a cell feature. For extraction of a nucleus size, the nucleus size is mainly obtained by calculating the area of each connected entity, that is, the nucleus, in the image according to a segmentation result of the nucleus. Moreover, for calculation of nucleus circularity, the nucleus circularity may be calculated by a formula: $e=(4\pi A1)/L^2$, where e represents the nucleus circularity, A1 represents the area of the nucleus, and L represents the perimeter of the nucleus. The density of the nucleus may be obtained by dividing the area of the nucleus by the area occupied by the nucleus in the corresponding feature obtaining region.

In Step S204, the method can obtain a feature of the duct tissue based on the cell features in the at least two feature obtaining regions. In this step, the image processing device 100 may use the cell feature, such as the cell structural feature and cell statistical feature of the cells of the duct tissue in the foregoing at least two feature obtaining regions, as the feature of the duct tissue. Moreover, this method for obtaining a feature of duct tissue may be adaptive to different morphological characteristics of the duct, to obtain the feature of the duct tissue with reference to a cytological feature and an intraductal structural feature.

In the foregoing method for obtaining a feature of duct tissue based on computer vision, first, the image processing device 100 obtains an image including duct tissue; and then determines, in an image region corresponding to the duct tissue in the image, at least two feature obtaining regions adapted to duct morphology of the duct tissue. Next, the image processing device 100 obtains cell features of cells of the duct tissue in the feature obtaining regions respectively. The image processing device 100 obtains a feature of the duct tissue based on the cell features of the cells of the duct tissue in the feature obtaining regions respectively. In the technical solutions provided in the embodiments of this application, the image processing device 100 may adaptively extract, based on morphological characteristics of various duct tissue, cell features from corresponding feature obtaining regions, and integrate the cell features of the regions to obtain a feature of the duct tissue, which can improve the accuracy of obtaining the feature of the duct tissue with reference to the cell feature and the duct morphological characteristic.

In an embodiment, before the determining, in an image region corresponding to the duct tissue in the image, at least two feature obtaining regions adapted to duct morphology of the duct tissue in step S202, the duct morphology of the duct tissue may be obtained in the following manner, specifically including using a boundary of the image region corresponding to the duct tissue in the image as a boundary of a duct tissue region, and determining the duct morphology of the duct tissue according to a boundary shape of the boundary of the duct tissue region.

In this embodiment, the image processing device 100 may determine, in the binarized image including the duct tissue, the boundary of the image region corresponding to the duct tissue according to the outer contour of the duct tissue, to obtain a boundary of the duct tissue region. Then, the image processing device 100 may obtain a boundary shape of the boundary of the duct tissue region. Exemplarily, the boundary shape may be a regular shape such as a circle or a square, or may be an irregular shape with some randomness. The image processing device 100 may determine the duct morphology of the duct tissue according to the boundary shape. For example, for some partial circular boundary shapes, the image processing device 100 may determine the duct morphology as a circle or an ellipse. The image processing device 100 may alternatively directly use the boundary shape as the duct morphology of the duct tissue. Through the solution of this embodiment, the image processing device 100 may quickly identify the duct morphology of the duct tissue according to the boundary of the duct tissue region, thereby helping to improve the efficiency of obtaining the feature of the duct tissue.

In an embodiment, the at least two feature obtaining regions adapted to duct morphology of the duct tissue may be both annular regions, boundary shapes of the annular regions being adapted to the duct morphology.

In this embodiment, an annular shape may be used as the shape of the feature obtaining region. That is, each feature obtaining region is an annular region. The annular region may be evenly distributed from the interior of the duct tissue to the boundary of the duct tissue. To be adaptive to different duct morphology of the duct tissue, the boundary shapes of the annular regions are adapted to the duct morphology. Exemplarily, the boundary shapes of an inner annular boundary and an outer annular boundary of the annular region may be the same as the boundary shape of the boundary of the duct tissue region. In this way, a region boundary of each feature obtaining region may be set parallel to the duct boundary, to better conform to the morphological characteristic of the duct tissue and improve the accuracy of feature obtaining.

Figure 3:
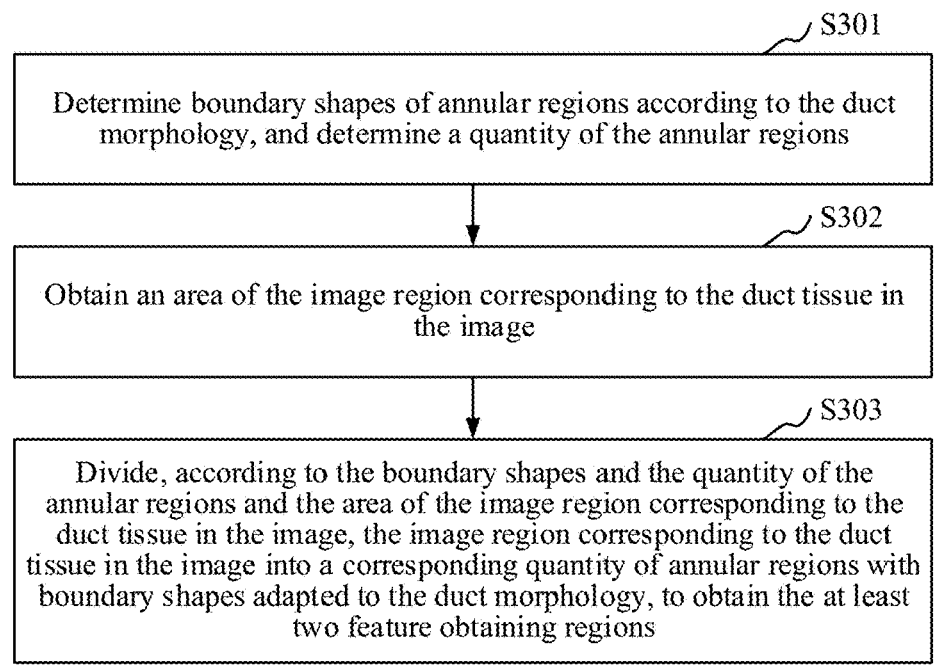
FIG. 3 is a schematic flowchart of steps of determining a feature obtaining region according to an embodiment.

In an embodiment, FIG. 3 is a schematic flowchart of steps of determining a feature obtaining region according to an embodiment. The determining, in an image region corresponding to the duct tissue in the image, at least two feature obtaining regions adapted to duct morphology of the duct tissue in step S202 may specifically include the following.

In Step S301, the method can determine the boundary shapes of the annular regions according to the duct morphology, and determine a quantity of the annular regions. In this step, the image processing device 100 may first determine the boundary shapes of the annular regions according to the duct morphology before dividing the feature obtaining regions, that is, use the annular regions as the feature obtaining regions. Moreover, the duct morphology may be determined according to the boundary shape of the boundary of the duct tissue region. The image processing device 100 may use the boundary shape of the boundary of the duct tissue region as the boundary shape of the annular region. In addition, the image processing device 100 further needs to determine the quantity of the annular regions. The quantity of the annular regions needs to be set to at least two, thereby dividing at least two feature obtaining regions from the image region corresponding to the duct tissue in the image for cell feature extraction.

In Step S302, the method can obtain an area of the image region corresponding to the duct tissue in the image. In this step, the image processing device 100 may obtain the area of the image region corresponding to the duct tissue in the image.

In Step S303, the method can divide, according to the boundary shapes and the quantity of the annular regions and the area of the image region corresponding to the duct tissue in the image, the image region corresponding to the duct tissue in the image into a corresponding quantity of annular regions with boundary shapes adapted to the duct morphology, to obtain the at least two feature obtaining regions. In this step, after determining the boundary shapes and quantity of the annular regions, and obtaining the area of the image region corresponding to the duct tissue in the image, the image processing device 100 performs feature obtaining region division on the image region corresponding to the duct tissue in the image. The image region is divided into a plurality of annular regions with a same quantity as described above and with boundary shapes the same as the boundary shape of the boundary of the duct tissue region as a feature obtaining regions for cell feature extraction.

The technical solutions of the foregoing embodiments provide a simple and feasible manner for determining a plurality of feature obtaining regions in the image region corresponding to the duct tissue in the image. By dividing the plurality of annular regions with boundary shapes the same as the boundary of the duct tissue region, the image processing device 100 may quickly obtain a plurality of feature obtaining regions applied to cell feature extraction. The annular regions further have a feature that the boundary is parallel to the boundary of the duct, which conforms to the morphological characteristic of the duct, so that the image processing device 100 acquires the feature of the duct tissue more accurately and stably.

To make the distribution of the annular regions more uniform, so as to obtain more accurate cell features in each annular region, thereby improving the accuracy of obtaining the feature of the duct tissue, in some embodiments, in a corresponding quantity of annular regions with boundary shapes adapted to the duct morphology, a same ring width may be set for the annular regions, to form uniform and multi-layered cell feature obtaining regions on the image.

The following provides a specific segmentation method for multi-layered annular regions, mainly including the following steps In Step A, the image processing device 100 determines a quantity n of annular regions, and calculate a size Ksize=2×sqrt(A2/π)/n of a morphological slider based on the quantity n of the annular regions, where A2 represents the area of the image region corresponding to the duct tissue in the image.

In Step B, the image processing device 100 sets a quantity of loop iterations to i=1, where an initial region is an entire duct region, when i<n, uses the slider defined in step A for performing a morphological erosion operation on a current region, and then obtains an annular region Ci by subtracting an eroded region from the current region, the eroded region being used as an initial region for a next iteration.

In Step C, the image processing device 100 may directly input the initial region as an innermost annular region when i=n, and end the loop.

The foregoing method of segmenting the annular region by using morphology has an advantage that the image processing device 100 may be directly adaptive different duct morphology, and boundaries of the annular regions obtained through segmentation are parallel to the boundary of the duct. At this time, the statistical feature of the duct tissue has a high consistency with the interpretation in the medical field.

In an embodiment, before the obtaining a feature of the duct tissue based on the cell features in the at least two feature obtaining regions in step S204, the method can further include the step of obtaining a sieve pore feature of sieve pores in the duct tissue based on the image region corresponding to the duct tissue in the image.

In this embodiment, mainly before obtaining the feature of the duct tissue, the image processing device 100 may further obtain another feature of the duct tissue in the image. For example, calcification and necrosis in the duct tissue may also be used as a basis for obtaining the feature of the duct tissue. In this embodiment, the image processing device 100 may further obtain a sieve pore feature of sieve pores in the duct tissue from the image region corresponding to the duct tissue in the image. The sieve pore feature of the sieve pore in the duct tissue is an important reference factor of obtaining the feature of the duct tissue. On the other hand, the sieve pore feature is also an important basis for medical identification of different intraductal proliferative lesions.

In an embodiment, the obtaining a feature of the duct tissue based on the cell features in the at least two feature obtaining regions in step S204 may further include that the image processing device 100 obtains the feature of the duct tissue according to the sieve pore feature and the cell features in the at least two feature obtaining regions.

In this embodiment, the image processing device 100 determines the feature of the duct tissue with reference to all of the sieve pore feature and the cell features in the at least two feature obtaining regions jointly, to improve the accuracy of obtaining the feature of the duct tissue. Exemplarily, in some embodiments, the sieve pore feature may include at least one of a sieve pore structural feature or a sieve pore statistical feature. The sieve pore structural feature is a basic feature of a single sieve pore such as a shape, a size and edge smoothness of the sieve pore. The sieve pore statistical feature is a statistical feature such as a quantity or distribution of sieve pores in the image region corresponding to the duct tissue in the image. In this way, the image processing device 100 may with reference to the sieve pore feature and cell features that are diverse to more accurately determine the feature of the duct tissue, which helps to subsequently precisely distinguish different types of duct tissue from other types of duct tissue.

Figure 4:
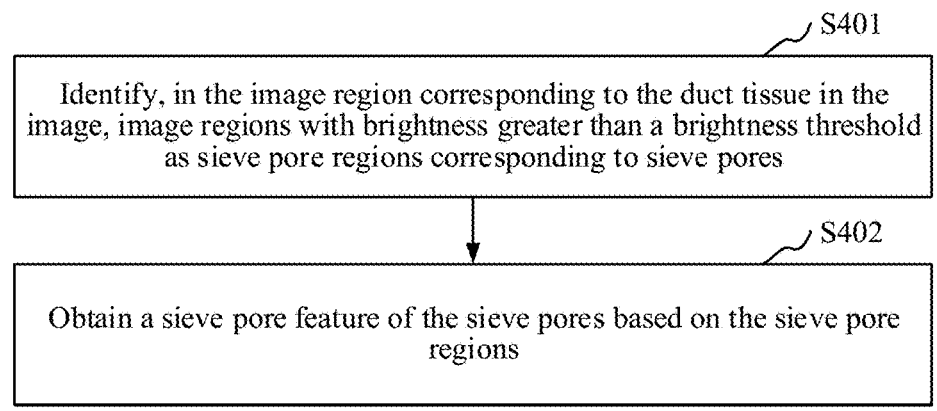
FIG. 4 is a schematic flowchart of steps of obtaining a sieve pore feature of sieve pores according to an embodiment.

In an embodiment, FIG. 4 is a schematic flowchart of steps of obtaining a sieve pore feature of sieve pores according to an embodiment. Based on the image region corresponding to the duct tissue in the image in the foregoing embodiments, the obtaining a sieve pore feature of sieve pores in the duct tissue may specifically include Step S401 of identifying, in the image region corresponding to the duct tissue in the image, image regions with brightness greater than a brightness threshold as sieve pore regions corresponding to the sieve pores.

In this step, the image processing device 100 may identify the sieve pore regions corresponding to the sieve pores from the image region corresponding to the duct tissue in the image. Specifically, the image processing device 100 may identify, in the image region corresponding to the duct tissue in the image, image regions with brightness greater than a brightness threshold as sieve pore regions corresponding to the sieve pores. The brightness threshold may be determined by the brightness of the cells of the duct tissue in the image. That is, the image processing device 100 may collect, in the duct tissue, statistics on brightness values of the cells of the duct tissue in the image, thereby setting a corresponding brightness threshold according to the brightness values of the cells in the image. When it is identified that the image region corresponding to the duct tissue in the image includes image regions with brightness greater than the brightness threshold, the image regions may be identified as sieve pore regions corresponding to the sieve pores, and the sieve pore regions may be identified without using an extra-image parameter.

To more precisely set the brightness threshold to accurately extract the sieve pore feature, in an embodiment, before the identifying, in the image region corresponding to the duct tissue in the image, image regions with brightness greater than a brightness threshold as sieve pore regions corresponding to the sieve pores in step S401, the brightness threshold may be set by obtaining nucleus brightness and cytoplasm brightness of the cells of the duct tissue in the image region corresponding to the duct tissue in the image, and obtaining the brightness threshold according to the nucleus brightness and the cytoplasm brightness.

Specifically, the image processing device 100 may identify nuclei and cytoplasm of cells of the duct tissue in the image region corresponding to the duct tissue in the image, collect statistics on brightness of the nuclei and cytoplasm of the cells in the image, and obtain the nucleus brightness and the cytoplasm brightness. Generally, the brightness of the sieve pore regions is usually higher than that of the nucleus and cytoplasm regions. In a specific scenario, the image processing device 100 may set the brightness threshold according to the calculation: Brightness threshold=2*Average value of cytoplasm brightness−Average value of nucleus brightness. That is, the image processing device 100 may determine the brightness threshold with reference to the average brightness of the nuclei and cytoplasm of the cells in the image, so that the sieve pore regions can be accurately identified by the image processing device 100.

In Step S402, the method can obtain the sieve pore feature of the sieve pores based on the sieve pore regions. In this step, after accurately determining the sieve pore regions at which the sieve pores are located, the image processing device 100 may use the feature of the sieve pore regions in the image as the sieve pore feature of the sieve pores. Specifically, the image processing device 100 may collect statistics on a quantity and distribution of the sieve pore regions in the image to obtain a sieve pore statistical feature, and may obtain a shape and size of each sieve pore region in the image to obtain a sieve pore structural feature.

Figure 5:
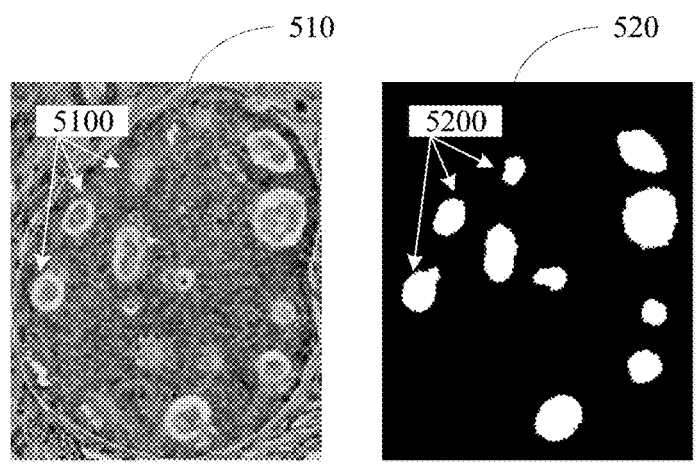
FIG. 5 is a schematic diagram of a sieve pore region extraction result according to an embodiment.

FIG. 5 is a schematic diagram of a sieve pore region extraction result according to an embodiment. The image processing device 100 may use a first exemplary image region 5100 of which brightness is higher than a brightness threshold set as above in a first exemplary image 510 as a sieve pore region. If a second exemplary image region 5200 shown in a second exemplary image 520 is a segmentation result of the sieve pore region corresponding to the first exemplary image region 5100, the image processing device 100 may obtain a sieve pore feature of a corresponding sieve pore according to the second exemplary image region 5200.

In an embodiment, after the obtaining a feature of the duct tissue based on the cell features in the at least two feature obtaining regions in step S204, a classification result of the duct tissue may further be obtained through the following step of obtaining, based on the feature of the duct tissue, a classification result of the duct tissue by using a duct classifier corresponding to a manner of dividing the feature obtaining regions in the image region.

In this embodiment, the image processing device 100 may classify the duct tissue based on the feature of the duct tissue, to obtain a classification result of the duct tissue. A duct tissue classifier may be used for classifying the duct tissue based on the feature of the duct tissue, and the duct tissue classifier may be obtained by training sample data based on an SVM model. It is to be understood that an increase in the amount of data may further improve the performance of the duct tissue classifier.

Moreover, the duct tissue classifier used in this embodiment may further be selected with reference to a manner of dividing the feature obtaining regions in the image region, because different manners of dividing the feature obtaining regions correspond to different features of the duct tissue. If the features of the duct tissue obtained by dividing the feature obtaining regions in different division manners by using a same type of duct tissue classifier, a classification result is not accurate. Specifically, the division manner may be dividing the feature obtaining regions using annular regions. Moreover, for the division manner of the annular regions, the annular regions may be further subdivided into different quantities of annular regions. That is, for division manners with different quantities of annular region, different duct tissue classifiers may be used to classify the duct tissue, thereby improving classification accuracy. For types of the duct tissue, exemplarily, for example, the types of a mammary duct may be divided into a normal duct, usual ductal hyperplasia (UDH), atypical ductal hyperplasia (ADH), ductal carcinoma in situ (DCIS), and the like.

Figure 6:
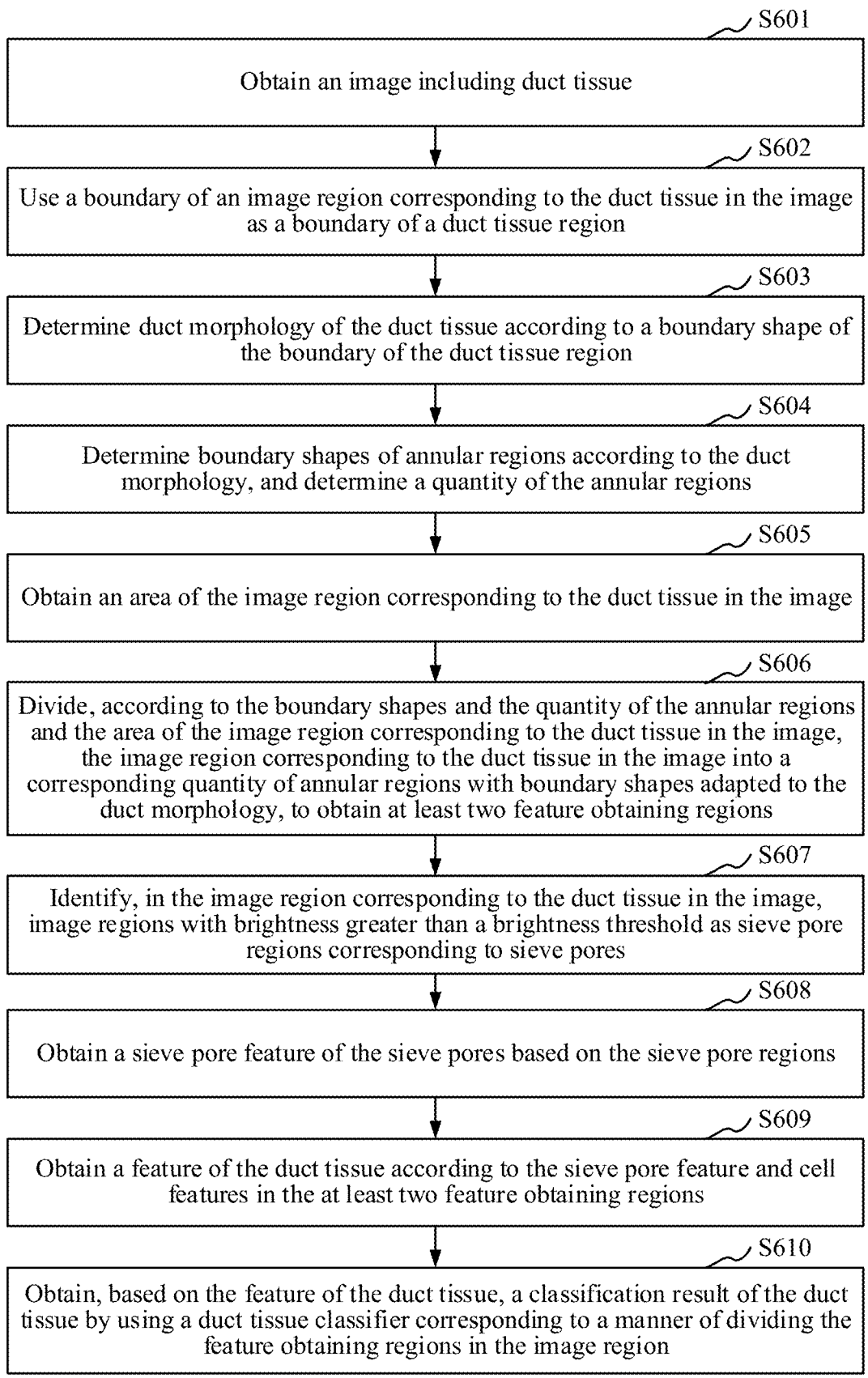
FIG. 6 is a schematic flowchart of a method for obtaining a feature of duct tissue based on computer vision according to another embodiment.

In an embodiment, a method for obtaining a feature of duct tissue based on computer vision is provided. FIG. 6 is a schematic flowchart of a method for obtaining a feature of duct tissue based on computer vision according to another embodiment. The method may be performed by the image processing device 100 shown in FIG. 1. The method for obtaining a feature of duct tissue based on computer vision may include the following steps.

In Step S601, the image processing device 100 obtains an image including duct tissue.

In Step S602, the image processing device 100 uses a boundary of the image region corresponding to the duct tissue in the image as a boundary of a duct tissue region.

In Step S603, the image processing device 100 determines duct morphology of the duct tissue according to a boundary shape of the boundary of the duct tissue region.

In Step S604, the image processing device 100 determines boundary shapes of annular regions according to the duct morphology, and determines a quantity of the annular regions.

In Step S605, the image processing device 100 obtains an area of the image region corresponding to the duct tissue in the image.

In Step S606, the image processing device 100 divides, according to the boundary shapes and the quantity of the annular regions and the area of the image region corresponding to the duct tissue in the image, the image region corresponding to the duct tissue in the image into a corresponding quantity of annular regions with boundary shapes adapted to the duct morphology, to obtain the at least two feature obtaining regions, the quantity of the annular regions being at least two.

In Step S607, the image processing device 100 identifies, in the image region corresponding to the duct tissue in the image, image regions with brightness greater than a brightness threshold as sieve pore regions corresponding to sieve pores.

In Step S608, the image processing device 100 obtains a sieve pore feature of the sieve pores based on the sieve pore regions.

In Step S609, the image processing device 100 obtains the feature of the duct tissue according to the sieve pore feature and the cell features in the at least two feature obtaining regions.

In Step S610, the image processing device 100 obtains, based on the feature of the duct tissue, a classification result of the duct tissue by using a duct classifier corresponding to a manner of dividing the feature obtaining regions in the image region.

In the foregoing method for obtaining a feature of duct tissue based on computer vision, the image processing device 100 may use computer vision to acquire an image of duct tissue, then, may adaptively extract, based on morphological characteristics of various duct tissue in the image, cell features from annular regions adapted to the duct morphology, and integrate the cell features of the regions and a sieve pore feature of the duct tissue to obtain the feature of the duct tissue. The image processing device 100 may further use a duct tissue classifier corresponding to a manner of dividing the annular regions in the image region to classify the duct tissue to obtain a corresponding classification result, thereby improving the accuracy of extracting the feature of the duct tissue and the accuracy of classifying the duct tissue.

It is to be understood that steps in the foregoing flowchart are displayed in sequence based on indication of arrows, but the steps are not necessarily performed in sequence based on a sequence indicated by the arrows. Unless clearly specified in this specification, there is no strict sequence limitation on the execution of the steps, and the steps may be performed in another sequence. Besides, at least some steps in the flowchart may include a plurality of sub-steps or a plurality of stages, the sub-steps or stages are not necessarily performed at a same moment and may be performed at different moments, the sub-steps or stages are not necessarily sequentially performed, and the sub-steps or stages and at least some of other steps or sub-steps or stages of other steps may be performed in turn or alternately.

The technical solution of this application is applied to a scenario of classifying a mammary duct in an HE-stained mammary pathological image for description, referring to FIG. 7 to FIG. 10.

Figure 7:
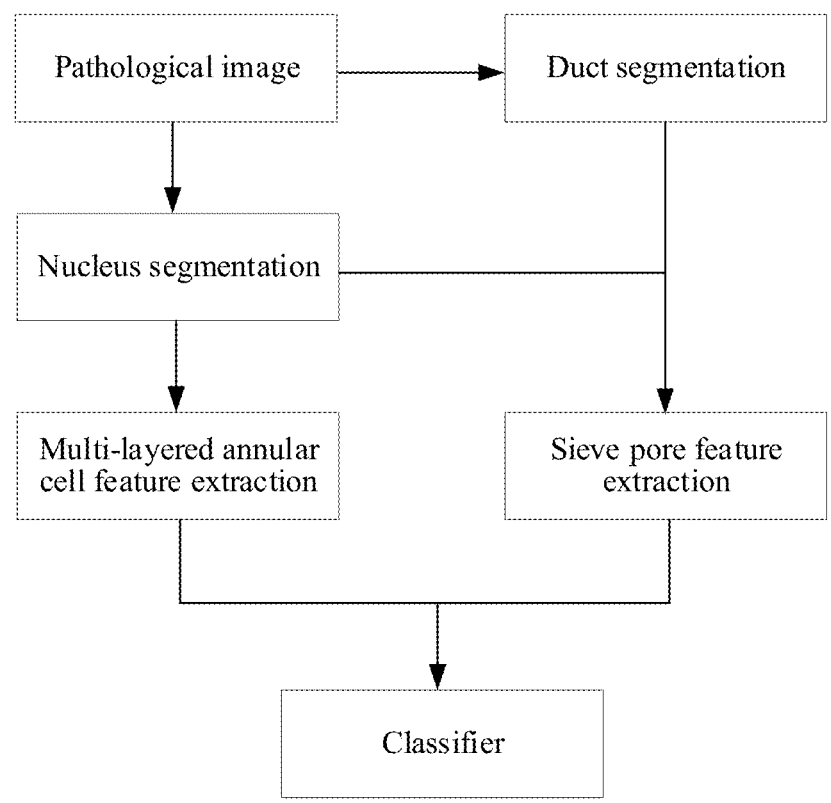
FIG. 7 is a schematic flowchart of a duct tissue classification method according to an application example.
Figure 8:
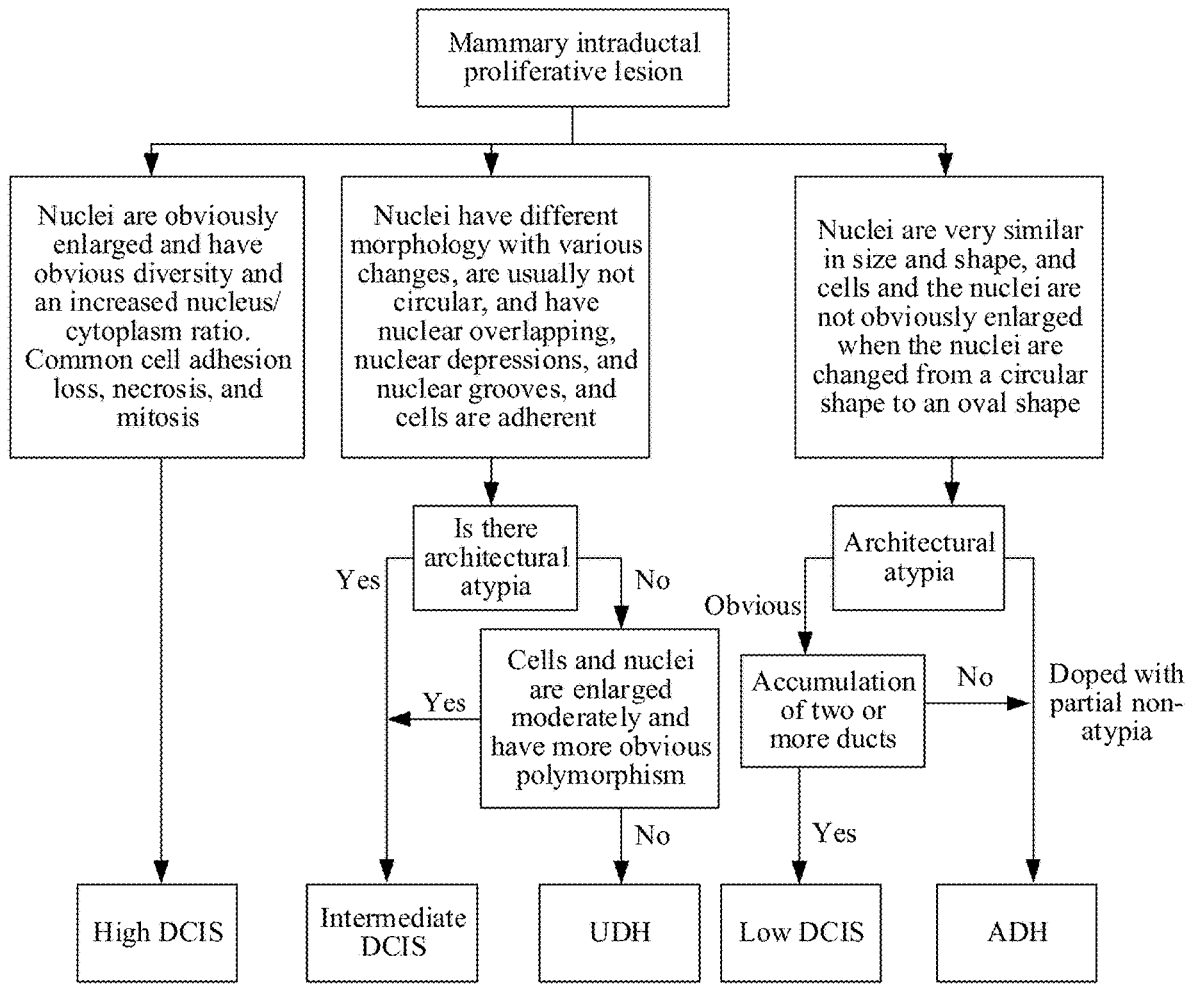
FIG. 8 is a schematic diagram of a reference flow for interpreting a type of duct tissue according to an application example.
Figure 10:
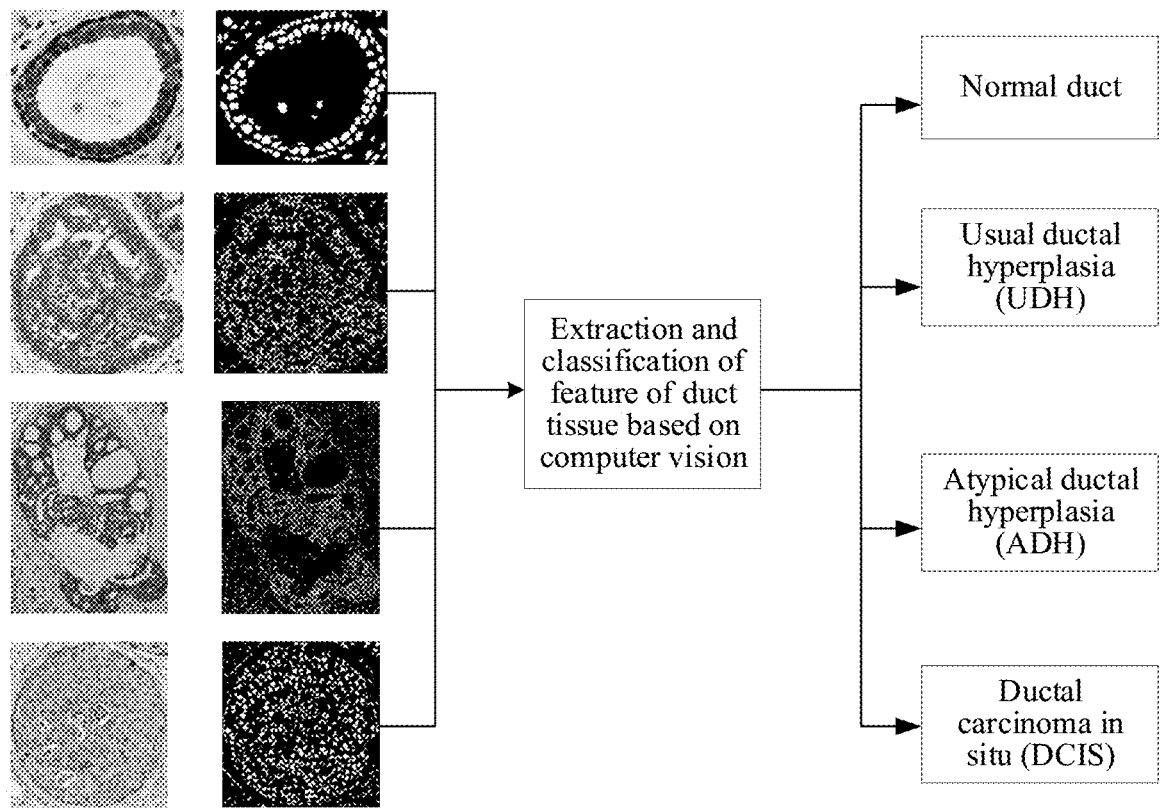
FIG. 10 is a schematic diagram of a result of interpreting a type of duct tissue according to an application example.

FIG. 10 is a schematic diagram of a result of interpreting a type of duct tissue according to an application example. In this application example, the mammary duct is classified by using a software interface. The input of the software interface is a segmented duct and a nucleus segmentation result in the HE-stained mammary pathological image, and the output of the software interface is an interpretation result of an intraductal proliferative lesion. Moreover, for an interpretation process of the intraductal proliferative lesion, reference may be made to FIG. 8. FIG. 8 is a schematic diagram of a reference flow for interpreting a type of duct tissue according to an application example. Based on the reference flow provided in FIG. 8 and with reference to the implementation of machine learning, a technical processing flow of an input image in this application example is shown in FIG. 7. FIG. 7 is a schematic flowchart of a duct tissue classification method according to an application example, which is described in detail as follows below.

For a segmentation module, including duct segmentation and nucleus segmentation, a deep neural network duct segmenter may be obtained based on a U-net segmentation network through training using a large quantity of samples, and a deep neural network nucleus segmenter may be obtained based on a mask-RCNN segmentation network through training using a large quantity of samples. Therefore, the current pathological image may be inputted into the two segmenters, to obtain duct and nucleus segmentation results. The nucleus segmentation result may be used for extracting a cell feature of the multi-layered annular regions, and the nucleus segmentation and duct segmentation results may be used together for extracting the sieve pore feature. The details of duct segmentation and nucleus segmentation are not limited herein provided that the duct and nucleus segmentation can be implemented on the image.

Cell feature extraction of multi-layered annular regions mainly includes the following.

(1) Extraction of a nucleus size:

For extraction of a nucleus size, the nucleus size is mainly obtained by calculating the area of each connected entity (the nucleus) according to a segmentation result of the nucleus.

(2) Calculation of nucleus circularity:

For calculation of nucleus circularity, the nucleus circularity may be calculated by the following formula: $e=(4\pi A1)/L^2$, where e represents the nucleus circularity, A1 represents the area of the nucleus, and L represents the perimeter of the nucleus.

(3) Calculation of density of the nucleus:

The density of the nucleus is obtained by dividing the area of the nucleus by the area of the annular region occupied.

(4) Extraction method for multi-layered annular regions:

Because the quantity of the nuclei in the duct tissue is relatively large, and the quantities and distributions of the nuclei in different ducts are different, the size, circularity, and density of the nucleus cannot be directly used. Based on statistics on features of different types of duct proliferation, and to adapt to differences in duct morphology, in this application example, a morphological method is used to segment the duct region into a plurality of annular regions. In the annular regions, statistics on statistical features, such as an average value and variance of nucleus sizes, statistical features such as an average value and variance of the cell circularity, a density feature of the nuclei in the annular regions, and the like are respectively collected.

For the segmentation method for the annular regions, the details are as follows.

In Step A, the segmentation method can determine a quantity n of the annular regions, and calculate a size $Ksize=2\times sqrt(A2/\pi)/n$ of a morphological slider size based on the quantity n of the annular region, where A2 represents the area of the image region corresponding to the duct tissue in the image.

In Step B, the segmentation method can set a quantity of loop iterations to i=1, where an initial region is an entire duct region, when i<n, use the slider defined in step A for performing a morphological erosion operation on a current region, and then obtain an annular region Ci by subtracting an eroded region from the current region, the eroded region being used as an initial region for a next iteration.

In Step C, the segmentation method can directly input the initial region as an innermost annular region when i=n, and end the loop.

An advantage of the foregoing morphological segmentation method is that the setting of the annular regions may be adaptive to the different duct morphology, so that the annular regions and boundary obtained through segmentation are parallel to the boundary of the duct. In this case, the feature obtained through statistics collection is highly consistent with the medical interpretation.

Figure 9:
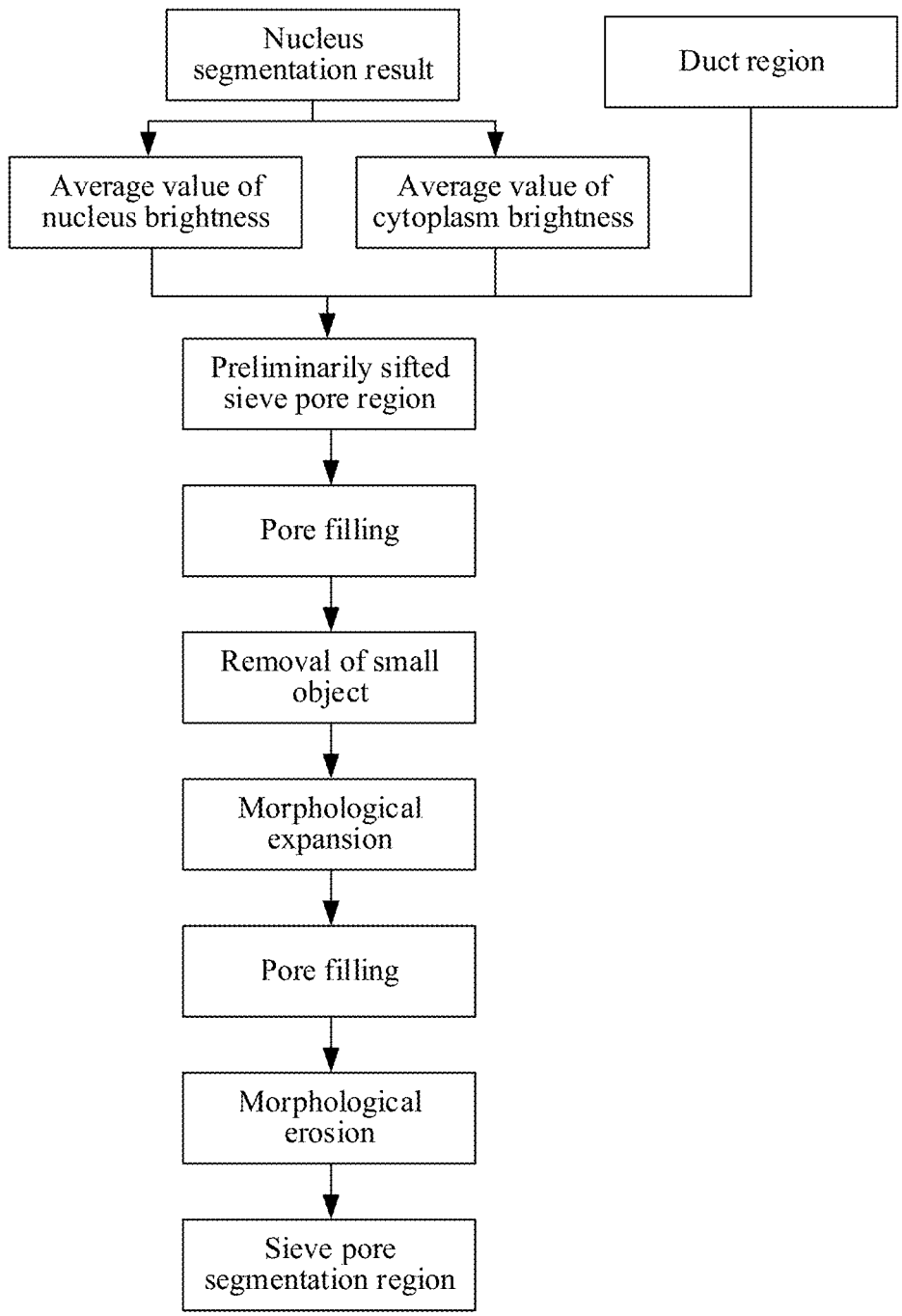
FIG. 9 is a schematic flowchart of a sieve pore region extraction method according to an application example.

For extraction of sieve pore features, sieve pore morphology is an important basis for differentiating different intraductal proliferative lesions. For the process of segmenting the sieve pore regions, reference may be made to FIG. 9. FIG. 9 is a schematic flowchart of a sieve pore region extraction method according to an application example. For a corresponding sieve pore region segmentation effect, reference may be made to FIG. 5. A preliminarily sifted sieve pore region is a region with brightness value higher than that of the nucleus and cytoplasm regions, and therefore, can be adjusted according to experience. An empirical threshold may be set to: 2*Average value of cytoplasm brightness−Average value of nucleus brightness. Specifically, the sieve pore feature may include a quantity of sieve pores and a circularity feature of each sieve pore. For circularity calculation, reference may be made to the calculation method of the nucleus circularity. In addition, a feature, such as edge smoothness of the sieve pore, may also be considered.

For the training of the classifier, the classifier may be trained using an SVM model. In a specific application scenario, the SVM model may be an RBF kernel, a regularization parameter is set to 1, and sample data used for training the model may include data of several cases of normal ducts, UDH, ADH, or DCIS. The samples may be reviewed and determined by experts in the medical field, and are kept consistent with the results of immunohistochemistry to ensure the accuracy of the training sample data. It is to be understood that an increase in the amount of sample data may further improve the performance of the classifier.

The solution for feature extraction and classification of duct tissue provided by the foregoing application examples has classification accuracy of 80% or more for the four types, namely, the normal duct, the UDH, the ADH, and the DCIS and classification accuracy of 90% or more for the two types, namely, the normal duct+the UDH and the ADH+the DCIS, thereby implementing automatic and accurate classification of an intraductal proliferative lesion according to a medical classification map by simultaneously using a cytological feature and an intraductal structural feature in combination with a learning SVM classifier. In addition, a multi-layered annular cytological feature extraction method is used, thereby extremely improving the accuracy and robustness of the feature extraction and the classification.

Figure 11:
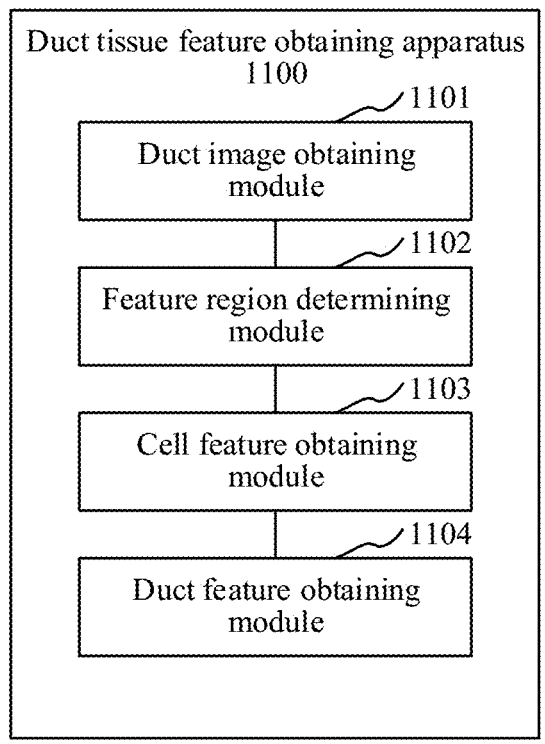
FIG. 11 is a structural block diagram of an apparatus for obtaining a feature of duct tissue based on computer vision according to an embodiment.

In an embodiment, an apparatus for obtaining a feature of duct tissue based on computer vision is provided. FIG. 11 is a structural block diagram of an apparatus for obtaining a feature of duct tissue based on computer vision according to an embodiment.

The duct tissue feature obtaining apparatus 1100 may include a duct image obtaining module 1101, configured to obtain an image including duct tissue, and a feature region determining module 1102, configured to determine, in an image region corresponding to the duct tissue in the image, at least two feature obtaining regions adapted to duct morphology of the duct tissue. The duct tissue feature obtaining apparatus 1100 can further include a cell feature obtaining module 1103, configured to obtain cell features of cells of the duct tissue in the at least two feature obtaining regions respectively, and a duct feature obtaining module 1104, configured to obtain a feature of the duct tissue based on the cell features in the at least two feature obtaining regions. Of course, it should be understood that one or more of the modules described in any of the exemplary embodiments of this disclosure can be implemented by hardware, such as processing circuitry, for example.

In an embodiment, the foregoing apparatus 1100 can further include a duct morphology determining module, configured to use a boundary of the image region corresponding to the duct tissue in the image as a boundary of a duct tissue region, and determine the duct morphology of the duct tissue according to a boundary shape of the boundary of the duct tissue region. In an embodiment, the at least two feature obtaining regions adapted to duct morphology of the duct tissue are both annular regions, boundary shapes of the annular regions being adapted to the duct morphology.

In an embodiment, the feature region determining module 1102 is further configured to determine the boundary shapes of the annular regions according to the duct morphology, and determine a quantity of the annular regions, the quantity being at least two, obtain an area of the image region corresponding to the duct tissue in the image, and divide, according to the boundary shapes and the quantity of the annular regions and the area of the image region corresponding to the duct tissue in the image, the image region corresponding to the duct tissue in the image into a corresponding quantity of annular regions with boundary shapes adapted to the duct morphology, to obtain the at least two feature obtaining regions.

In an embodiment, the corresponding quantity of annular regions with boundary shapes adapted to the duct morphology have a same ring width. In an embodiment, the cell features of cells of the duct tissue in the at least two feature obtaining regions respectively include at least one of a cell statistical feature or a cell structural feature of cells in a corresponding feature obtaining region.

In an embodiment, the foregoing apparatus 1100 further includes: a sieve pore feature obtaining module, configured to obtain a sieve pore feature of sieve pores in the duct tissue based on the image region corresponding to the duct tissue in the image. The duct feature obtaining module 1104 is further configured to obtain the feature of the duct tissue based on the sieve pore feature and the cell features in the at least two feature obtaining regions.

In an embodiment, the sieve pore feature obtaining module, can be further configured to identify, in the image region corresponding to the duct tissue in the image, image regions with brightness greater than a brightness threshold as sieve pore regions corresponding to the sieve pores, the brightness threshold being determined according to brightness of the cells in the image, and obtain the sieve pore feature of the sieve pores based on the sieve pore regions.

In an embodiment, the sieve pore feature obtaining module can be further configured to obtain, before the identifying, in the image region corresponding to the duct tissue in the image, image regions with brightness greater than a brightness threshold as sieve pore regions corresponding to the sieve pores, nucleus brightness and cytoplasm brightness of the cells of the duct tissue in the image region corresponding to the duct tissue in the image; and obtain the brightness threshold according to the nucleus brightness and the cytoplasm brightness.

In an embodiment, the sieve pore feature includes at least one of a sieve pore structural feature or a sieve pore statistical feature. In an embodiment, the foregoing apparatus 1100 further includes a duct classification module, configured to obtain, based on the feature of the duct tissue, a classification result of the duct tissue by using a duct tissue classifier corresponding to a manner of dividing the feature obtaining regions in the image region.

Figure 12:
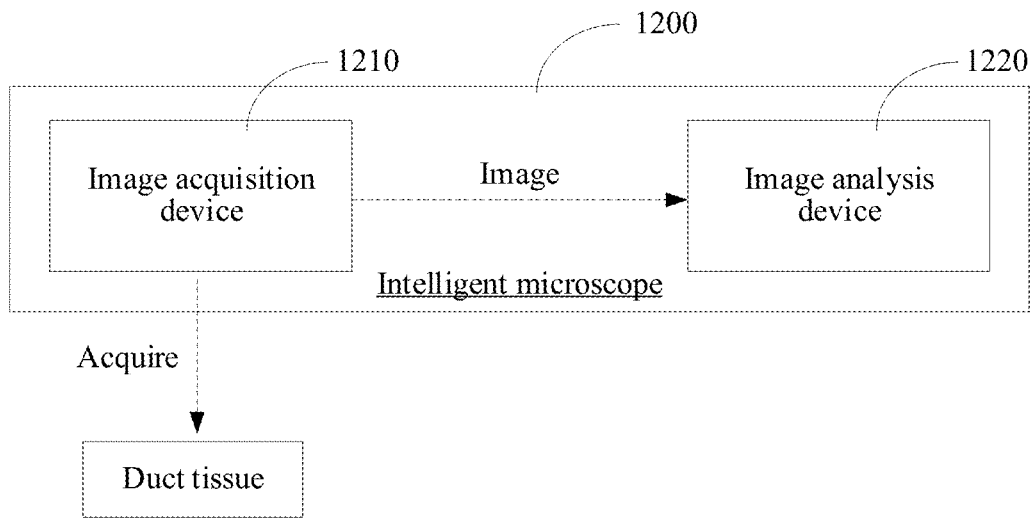
FIG. 12 is a structural block diagram of an intelligent microscope according to an embodiment.

In an embodiment, an intelligent microscope is provided. FIG. 12 is a structural block diagram of an intelligent microscope 1200 according to an exemplary embodiment. The intelligent microscope 1200 may include an image acquisition device 1210 and an image analysis device 1220.

The image acquisition device 1210 can be configured to obtain an image including duct tissue; and transmit the image to the image analysis device 1220.

The image analysis device 1220 is configured to perform the steps of the method described in any one of the foregoing embodiments.

The intelligent microscope provided in the foregoing embodiments may be applied to feature extraction on duct tissue, such as a mammary duct. The image acquisition device 1210 acquires an image including mammary ducts with various morphological characteristics, and transfer them to the image analysis device 1220 for feature extraction. The image analysis device 1220 may be equipped with a processor with an image processing function. The processor performs the step of the method for obtaining a feature of duct tissue based on computer vision in any one of the foregoing embodiments, to perform feature extraction on the mammary ducts with various morphological characteristics, and identify the intraductal proliferative lesion according to extracted features, thereby improving the accuracy of feature extraction and the lesion identification.

Figure 13:
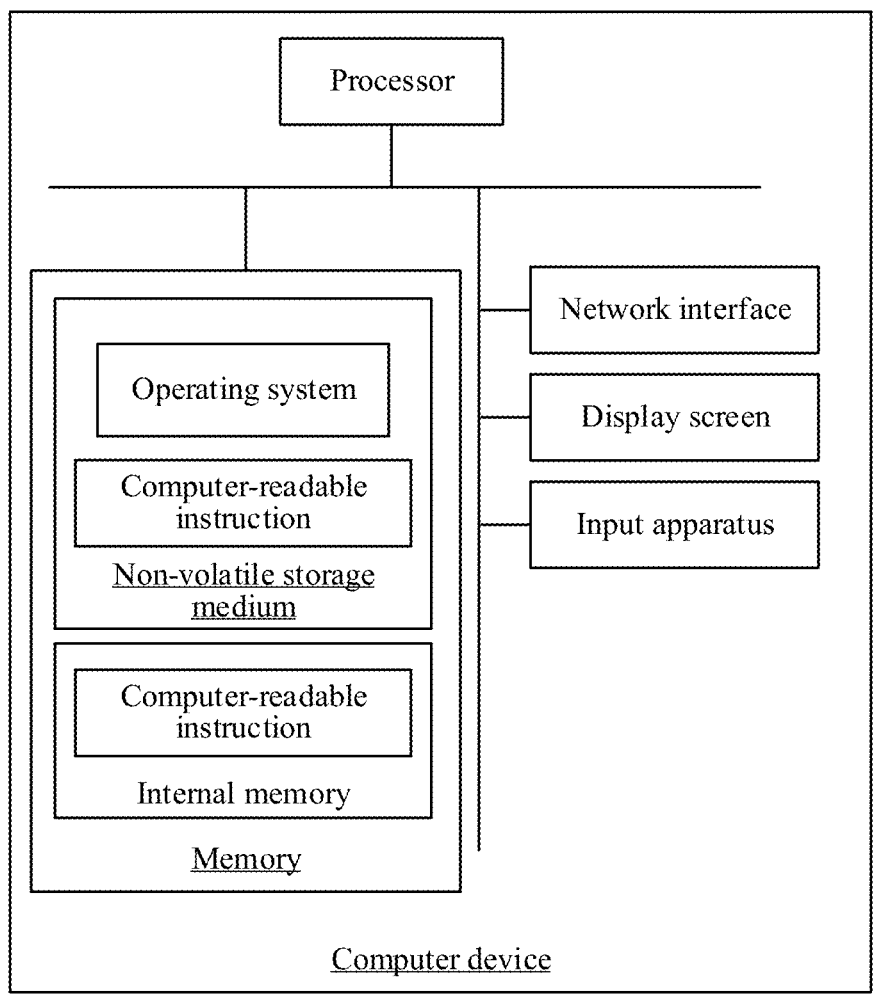
FIG. 13 is a structural block diagram of a computer device according to an embodiment.

FIG. 13 is a structural block diagram of a computer device according to an embodiment. The computer device may be specifically the image processing device 100 shown in FIG. 1. As shown in FIG. 13, the computer device includes a processor, a memory, a network interface, an input apparatus, and a display screen that are connected by a system bus. The memory includes a non-volatile storage medium and an internal memory. The non-volatile storage medium of the computer device stores an operating system, and may further store non-transitory computer-readable instructions. The non-transitory computer-readable instructions, when executed by the processor, may cause the processor to implement a method for obtaining a feature of duct tissue based on computer vision. The internal memory may also store non-transitory computer-readable instructions. The non-transitory computer-readable instructions, when executed by the processor, may cause the processor to implement the method for obtaining a feature of duct tissue based on computer vision. The display screen of the computer device may be a liquid crystal display screen or an electronic ink display screen. The input apparatus of the computer device may be a touch layer covering the display screen, or may be a key, a trackball, or a touch pad disposed on a housing of the computer device, or may be an external keyboard, a touch pad, a mouse, or the like.

A person skilled in the art may understand that, the structure shown in FIG. 13 is only an exemplary block diagram of a part of a structure related to a solution of this application and does not limit the computer device to which the solution of this application is applied. Specifically, the computer device may include more or fewer components than those in the drawings, or include a combination of some components, or include different component layouts.

In an embodiment, a computer device is provided, including a memory and a processor. The memory stores non-transitory computer-readable instructions, the non-transitory computer-readable instructions, when executed by the processor, causing the processor to perform the steps of the foregoing method for obtaining a feature of duct tissue based on computer vision. The steps of the method for obtaining a feature of duct tissue based on computer vision herein may be the steps in the method for obtaining a feature of duct tissue based on computer vision of the foregoing various embodiments.

In an embodiment, a non-transitory computer-readable storage medium is provided. The non-transitory computer-readable storage medium stores computer-readable instructions, the computer-readable instructions, when executed by the processor, causing the processor to perform the steps of the foregoing method for obtaining a feature of duct tissue based on computer vision. The steps of the method for obtaining a feature of duct tissue based on computer vision herein may be the steps in the method for obtaining a feature of duct tissue based on computer vision of the foregoing various embodiments.

In an embodiment, a non-transitory computer-readable instruction product or non-transitory computer-readable instructions are provided, the non-transitory computer-readable instructions product or the non-transitory computer-readable instructions include computer instructions, and the computer instructions are stored in the non-transitory computer-readable storage medium. The processor of the computer device reads the computer instructions from the non-transitory computer-readable storage medium, and the processor executes the computer instructions, to cause the computer device to perform the steps in the foregoing method embodiments.

A person of ordinary skill in the art may understand that all or some of the procedures of the methods of the foregoing embodiments may be implemented by non-transitory computer-readable instructions instructing relevant hardware. The non-transitory computer-readable instructions may be stored in a non-volatile computer-readable storage medium. When the non-transitory computer-readable instructions are executed, the procedures of the embodiments of the foregoing methods may be included. Any reference to a memory, a storage, a database, or another medium used in the embodiments provided in this application may include at least one of a non-volatile memory and a volatile memory. The non-volatile memory may include a read-only memory (ROM), a magnetic tape, a floppy disk, a flash memory, an optical memory, and the like. The volatile memory may include a random access memory (RAM) or an external cache. For the purpose of description instead of limitation, the RAM is available in a plurality of forms, such as a static RAM (SRAM) or a dynamic RAM (DRAM).

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

The foregoing embodiments show only several implementations of this application and are described in detail, which, however, are not to be construed as a limitation to the patent scope of this application. A person of ordinary skill in the art may further make several variations and improvements without departing from the ideas of this application, and such variations and improvements all fall within the protection scope of this application. Therefore, the protection scope of this application shall be subject to the protection scope of the appended claims.

What is claimed is:

1. A method for obtaining a feature of duct tissue based on computer vision, the method comprising:
obtaining an image that includes the duct tissue;
determining at least two feature obtaining regions that are adapted to duct morphology of the duct tissue in an image region corresponding to the duct tissue in the image;
obtaining cell features of cells of the duct tissue in the at least two feature obtaining regions, respectively;
identifying image sub-regions with brightness greater than a brightness threshold as sieve-like pore regions in the image region corresponding to the duct tissue;
obtaining a feature of sieve-like pores in the duct tissue based on the image sub-regions of the image region corresponding to the duct tissue in the image;
obtaining the feature of the duct tissue based on the feature of the sieve-like pores and the cell features in the at least two feature obtaining regions;
selecting, from a plurality of duct tissue classifiers associated with different division methods of the image region, a duct tissue classifier based on which division method of the different division methods is used for determining the at least two feature obtaining regions; and classifying the duct tissue using the selected duct tissue classifier based on the obtained feature of the duct tissue.

2. The method according to claim 1, wherein before the determining the at least two feature obtaining regions adapted to duct morphology of the duct tissue, the method further comprises:

using a boundary of the image region corresponding to the duct tissue in the image as a boundary of a duct tissue region; and determining the duct morphology of the duct tissue based on a boundary shape of the boundary of the duct tissue region.

3. The method according to claim 1, wherein the at least two feature obtaining regions adapted to duct morphology of the duct tissue are both annular regions with boundary shapes of the annular regions that are adapted to the duct morphology.

4. The method according to claim 3, wherein the determining the at least two feature obtaining regions adapted to duct morphology of the duct tissue further comprises:

determining the boundary shapes of the annular regions based on the duct morphology and determining a quantity of the annular regions, the quantity being at least two;

obtaining an area of the image region corresponding to the duct tissue in the image; and dividing the image region corresponding to the duct tissue in the image into a corresponding quantity of annular regions with boundary shapes adapted to the duct morphology to obtain the at least two feature obtaining regions based on the boundary shapes and the quantity of the annular regions and the area of the image region corresponding to the duct tissue in the image.

5. The method according to claim 4, wherein the corresponding quantity of annular regions with boundary shapes adapted to the duct morphology have a same ring width.

6. The method according to claim 1, wherein the cell features of the cells of the duct tissue in the at least two feature obtaining regions respectively include at least one of a cell statistical feature or a cell structural feature of the cells in a corresponding feature obtaining region.

7. The method according to claim 1, wherein the obtaining the feature of the sieve-like pores in the duct tissue further comprises:

determining the brightness threshold based on brightness of the cells in the image.

8. The method according to claim 1, wherein before the identifying the image sub-regions with the brightness greater than the brightness threshold, the method further comprises:

obtaining nucleus brightness and cytoplasm brightness of the cells of the duct tissue in the image region corresponding to the duct tissue in the image; and obtaining the brightness threshold based on the nucleus brightness and the cytoplasm brightness.

9. The method according to claim 1, wherein the feature of the sieve-like pores comprises at least one of a sieve-like pore structural feature or a sieve-like pore statistical feature.

10. An intelligent microscope, comprising an image acquisition device and an image analysis device, wherein:

the image acquisition device is configured to obtain an image comprising duct tissue and transmit the image to the image analysis device, and the image analysis device is configured to perform the method according to claim 1.

11. A computer device comprising a memory and a processor, the memory storing non-transitory computer-readable instructions that, when executed by the processor, cause the processor to perform the method according to claim 1.

12. An apparatus for obtaining a feature of duct tissue based on computer vision, the apparatus comprising processing circuitry that is configured to:

obtain an image including the duct tissue;

determine at least two feature obtaining regions adapted to duct morphology of the duct tissue in an image region corresponding to the duct tissue in the image;

obtain cell features of cells of the duct tissue in the at least two feature obtaining regions, respectively;

identify image sub-regions with brightness greater than a brightness threshold as sieve-like pore regions in the image region corresponding to the duct tissue;

obtain a feature of sieve-like pores in the duct tissue based on the image sub-regions of the image region corresponding to the duct tissue in the image;

obtain the feature of the duct tissue based on the feature of the sieve-like pores and the cell features in the at least two feature obtaining regions;

select, from a plurality of duct tissue classifiers associated with different division methods of the image region, a duct tissue classifier based on which division method of the different division methods is used for determining the at least two feature obtaining regions; and classify the duct tissue using the selected duct tissue classifier based on the obtained feature of the duct tissue.

13. A non-transitory computer-readable storage medium that stores instructions which, when executed by a processor, cause the processor to perform operations comprising:

obtaining an image that includes duct tissue;

determining at least two feature obtaining regions that are adapted to duct morphology of the duct tissue in an image region corresponding to the duct tissue in the image;

obtaining cell features of cells of the duct tissue in the at least two feature obtaining regions, respectively;

identifying image sub-regions with brightness greater than a brightness threshold as sieve-like pore regions in the image region corresponding to the duct tissue;

obtaining a feature of sieve-like pores in the duct tissue based on the image sub-regions of the image region corresponding to the duct tissue in the image;

obtaining a feature of the duct tissue based on the feature of the sieve-like pores and the cell features in the at least two feature obtaining regions;

selecting, from a plurality of duct tissue classifiers associated with different division methods of the image region, a duct tissue classifier based on which division method of the different division methods is used for determining the at least two feature obtaining regions; and classifying the duct tissue using the selected duct tissue classifier based on the obtained feature of the duct tissue.

14. The non-transitory computer-readable storage medium according to claim 13, wherein before the determining the at least two feature obtaining regions adapted to duct morphology of the duct tissue, the processor performs operations further comprising:

using a boundary of the image region corresponding to the duct tissue in the image as a boundary of a duct tissue region; and determining the duct morphology of the duct tissue based on a boundary shape of the boundary of the duct tissue region.

15. The non-transitory computer-readable storage medium according to claim 13, wherein the at least two feature obtaining regions adapted to duct morphology of the duct tissue are both annular regions with boundary shapes of the annular regions that are adapted to the duct morphology.

16. The non-transitory computer-readable storage medium according to claim 15, wherein the determining the at least two feature obtaining regions adapted to duct morphology of the duct tissue further comprises:

determining the boundary shapes of the annular regions based on the duct morphology and determining a quantity of the annular regions, the quantity being at least two;

obtaining an area of the image region corresponding to the duct tissue in the image; and dividing the image region corresponding to the duct tissue in the image into a corresponding quantity of annular regions with boundary shapes adapted to the duct morphology to obtain the at least two feature obtaining regions based on the boundary shapes and the quantity of the annular regions and the area of the image region corresponding to the duct tissue in the image.

17. The non-transitory computer-readable storage medium according to claim 16, wherein the corresponding quantity of annular regions with boundary shapes adapted to the duct morphology have a same ring width.

18. The non-transitory computer-readable storage medium according to claim 13, wherein the cell features of the cells of the duct tissue in the at least two feature obtaining regions respectively include at least one of a cell statistical feature or a cell structural feature of the cells in a corresponding feature obtaining region.

\* \* \* \* \*